United States Patent
Ghanbari et al.

(10) Patent No.: US 11,369,717 B2
(45) Date of Patent: Jun. 28, 2022

(54) FIBROUS NERVE CONDUIT FOR PROMOTING NERVE REGENERATION

(71) Applicants: Hossein Ghanbari, Tehran (IR); Niloofar Nazeri, Tehran (IR)

(72) Inventors: Hossein Ghanbari, Tehran (IR); Niloofar Nazeri, Tehran (IR)

(*) Notice: Subject to any disclaimer, the term of this patent is extended or adjusted under 35 U.S.C. 154(b) by 241 days.

(21) Appl. No.: 16/895,308

(22) Filed: Jun. 8, 2020

(65) Prior Publication Data
US 2020/0384157 A1  Dec. 10, 2020

(51) Int. Cl.
*A61L 27/36* (2006.01)
*A61L 27/22* (2006.01)
*A61L 27/38* (2006.01)

(52) U.S. Cl.
CPC .......... *A61L 27/3675* (2013.01); *A61L 27/225* (2013.01); *A61L 27/227* (2013.01); *A61L 27/3878* (2013.01); *A61L 2400/12* (2013.01); *A61L 2430/32* (2013.01)

(58) Field of Classification Search
None
See application file for complete search history.

*Primary Examiner* — Hasan S Ahmed
*Assistant Examiner* — Randeep Singh
(74) *Attorney, Agent, or Firm* — Barry Choobin; Patent 360

(57) ABSTRACT

The present invention relates to a fibrous nerve conduit for promoting nerve regeneration, comprising a channel, the channel having diameter controllable ends, the channel is adjustable to suturing to a proximal and distal end of a severed nerve, the conduit further comprises a PCL (MW: 70KDa) with concentration of 10-15% and PLGA (MW: 50KDa,50:50) with concentration of 10-18%.

8 Claims, 6 Drawing Sheets

FIBROUS NERVE CONDUIT FOR PROMOTING NERVE REGENERATION

FIELD OF THE INVENTION

The present invention relates to the field of neurology. More specifically, design and fabrication of nerve conduits for use in nerve regeneration. In particular, the invention relates to design the aligned nerve conduits.

BACKGROUND OF THE INVENTION

Nerve injuries impose a burden on the health-care systems all over the world. Although some of nerve gaps became repaired through the natural repair mechanisms of peripheral nerve system, many of them need to be repaired surgically in order to regenerate a damaged nerve. The methods of treatment seem to depend on the size of the injury. When end-to-end tensionless neurorraphy is not possible, an autologous nerve grafts are the best standard option for nerve repair. However, a problem in donor-site such as neuroma formation and permanent loss of sensation necessitates investigation of alternative methods.

U.S. Pat. No. 3,960,151A discloses about a method and means for the repair of severed peripheral nerves utilizing a porous, thin walled, bridge conduit or tube and an applicator instrument thereof. The instrument is connected to a vacuum source and has means for supporting the tube in the region of the transverse hole therein. When supported by the instrument the interior of the tube is operatively connected to the vacuum source through the transverse hole and a pressure differential is created between the interior of the tube and the ambient atmosphere by means of the vacuum source. This pressure differential is used to draw one end of the severed nerve into one end of the tube and then the other end of the severed nerve into the other end of the tube, the nerve ends being in abutment within the tube. Additional means may be provided to maintain the nerve ends in abutment within the tube when required and means may also be provided facilitating removal of the tube upon repair of the nerve if desired.

The disadvantage of the prior art is that the invention only helps the two ends of broken nerve to come closer for joining the two ends. The process takes a long period of time in joining the nerve conduit. The invention does not provide any boost in growing the nerve to attach the broken ends.

In recent years, the repair and regeneration of nerve through tissue engineering have been attracted attentions. Neural tissue engineering involves outgrowth of nerve in artificial nerve conduits made from different polymers. Thereby, polymeric biomaterials play an important role in tissue engineering with/without living precursor cells. A variety of natural and synthetic polymers such as Poly (3-caprolactone) (PCL), poly (L-lactic co glycolic acid) (PLGA) and collagen have been used in nerve regeneration approaches.

According to recent patents, another mainly ignored parameter is the matching between diameter of the conduit lumen and the damaged nerve. Damaged nerve stumps are sutured to the edges of the conduit to provide a protected microenvironment. In this micro environment a fibrin matrix can form between the nerve stumps and act as a scaffold. The scaffold support migration of Schwann cells and axons trailing which induced by neurogenic and trophic factors. An oversized or poorly fitting conduit adversely affects fibrin stability and consequently leads to less predictable clinical results. In other states, poorly fitting conduit cannot protect neuro supportive factors presented in microenvironment and results in loss of the crucial fibrin clot.

KR101116237B1 discloses about a silk nano-fiber neural conduit having pores formed by entangled silk nano-fibers having a diameter of about 200 to 400 nm prepared by producing a silk fiber spinning stock solution from silk fibers and then electro-spinning the same, Specifically, preparing a fiber spinning stock solution (step 1); Preparing a conduit-shaped silk nano-fiber by electro-spinning the fiber spinning stock solution prepared in step 1 to a collector coated with polyethylene oxide (PEO) (step 2); And separating the conduit-shaped silk nano-fibers prepared in step 2 from the collection unit (step 3). According to the present invention, the silk nano-fiber nerve conduit not only has excellent biocompatibility, but also allows fluid to be exchanged between the inside and the outside of the conduit through pores, and has proper elasticity, tensile strength and tear strength, thereby helping to regenerate damaged nerves. It can be very useful for treating damaged nerves in place of existing synthetic polymer neuron conduits because it shows excellent neuronal regeneration effect by restoring motor and sensory functions. Nerve conduit, silk nano-fiber, electro-spinning, nerve regeneration, sensory recovery, exercise recovery The disadvantage of the prior art is that the invention does not provide topographical cues for regenerating axons. Another problem is that the invention only repair nerve of a particular size as the artificial conduit consists of fixed size diameter so the nerve smaller or larger than the artificial conduit may not be regenerated.

To overcome the problem of matching the size of the artificial conduit with the nerve conduit, there is a need to develop an artificial conduit which should be compatible with all the sizes of the nerves.

OBJECTS OF THE INVENTION

The principal object of the present invention is to overcome the disadvantages of the prior art.

An object of the present invention is to regenerate a broken nerve by joining a fibrous nerve conduit.

Another object of the present invention is to provide a size adjustable nerve conduit for joining nerves of different sizes.

The foregoing and other objects, features, and advantages of the present invention will become readily apparent upon further review of the following detailed description of the preferred embodiment as illustrated in the accompanying drawings.

SUMMARY OF THE INVENTION

The present invention contemplates about a nerve conduit from aligned nano-fibers with random ends to increase mechanical properties in order to provide better attachment.

According to an embodiment of the present invention, fibrous nerve conduit for promoting nerve regeneration, comprising a channel, the channel having diameter controllable ends with adjustable diameter from 0.1 to 10 cm, wherein the ends prevent conduit collapse during and after surgery due to their conical shape and random alignment. The channel is adjustable to suturing to a proximal and distal end of a severed nerve. The conduit further comprises a PCL (MW: 70 KDa) with concentration of 10-15% and PLGA (MW: 50 KDa, 50:50) with concentration of 10-18%.

While the invention has been described and shown with reference to the preferred embodiment, it will be apparent that variations might be possible that would fall within the scope of the present invention.

BRIEF DESCRIPTION OF THE DRAWINGS

Embodiments of the present disclosure will now be described, by way of example only, with reference to the following diagrams wherein.

DETAILED DESCRIPTION OF THE INVENTION

The following description includes the preferred best mode of one embodiment of the present invention. It will be clear from this description of the invention that the invention is not limited to these illustrated embodiments but that the invention also includes a variety of modifications and embodiments thereto. Therefore, the present description should be seen as illustrative and not limiting. While the invention is susceptible to various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

In any embodiment described herein, the open-ended terms "comprising," "comprises," and the like (which are synonymous with "including," "having" and "characterized by") may be replaced by the respective partially closed phrases "consisting essentially of," "consists essentially of," and the like or the respective closed phrases "consisting of," "consists of, the like.

As used herein, the singular forms "a," "an," and "the" designate both the singular and the plural, unless expressly stated to designate the singular only.

The present invention talks about designing for conduits fabricated by modified air gap electro-spinning to bridge between tubular structures that such as damaged nerves.

Figure 1:
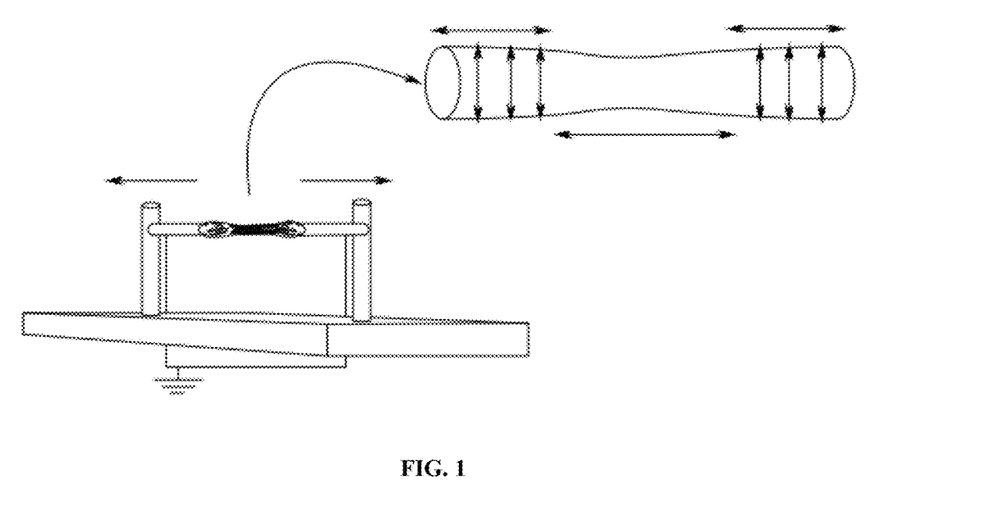
FIG. 1 illustrates a schematic view of the fibrous nerve conduit for promoting nerve regeneration, showing electro-spinning collector and a nerve conduit FIG. 2. illustrates a pictorial representation of the fibrous nerve conduit for promoting nerve regeneration, showing PLGA/PCL-CNT nano-fibers.
Figure 2:
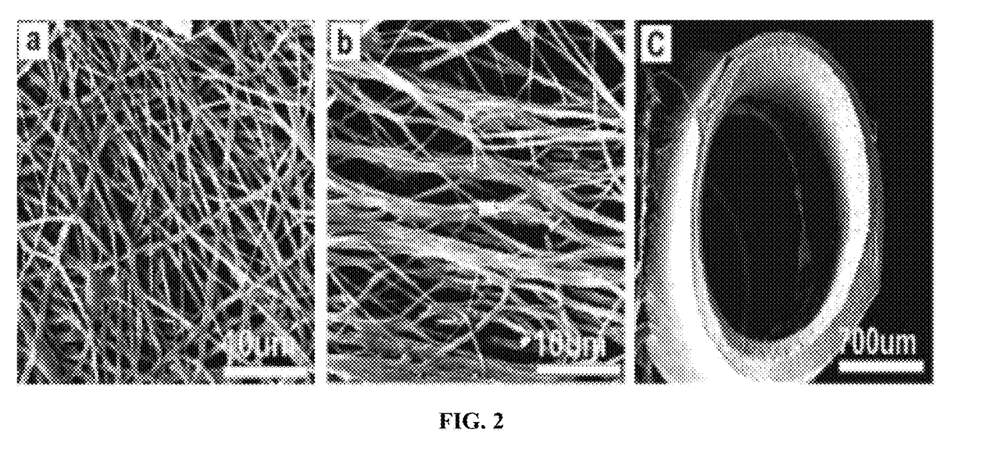

Referring to FIG. 1, illustrates schematic view of the conduit fabrication. The setup of the invention is comprises of a syringe pump to deliver polymer solution to the tip of a needle and a channel with adjustable distance. The channel is preferably cylindrical in shape with aligned fibers. The channel has ability to adjust the gap size by pulling the channel from the sides. Electro-spinning solutions is charged to 14-17 kV and directed into the collector that is grounded.

Due to electrical charge, fibers are drawn to the collector and some of them deposited with random alignment and others bridged across the gap to form the hollow channel with aligned fibers in the middle part. Different polymer solutions such as PLGA/PCL-CNT and PCL/Collagen are used to produce new-design nerve conduit. The concentration of PCL (MW: 70 KDa) is 10-15% (w/v) and the concentration of PLGA (MW: 50 KDa, 50:50) is 10-18% (w/v). The CNT may include but not limited to single wall, double wall or multi wall. The conduit produced in different length in different parts that means the middle part and conical ends may produced in different length independently, the length for each of them can be at least 1 mm to about 5 cm. The conduit carry agents that may include but not limited to protein solutions, drugs, gels and alike.

The PCL-PLGA/CNT nano-fibers comprise about 10 to 90% by weight PCL and about 90 to 10% by weight PLGA and the weight of MWCNT to polymers is 0.1-1%. PCL and PLGA are miscible in different solvents such as chloroform and HFIP and MWCNT is completely dispersible in them. The PCL-PLGA/CNT nano-fibers consists of various diameters between the range of 100-800 nm that is ideal for nerve regeneration. When the nerve stumps is introduced into the nerve conduit the nerve tissue grows in the conduit from proximal to distal end. The growth is along conduit lumen formed in the middle of the electro-spun fibers. Due to fibers alignment in the middle part of the nerve conduit, growth cone would be directed from proximal to distal stump and regenerated axons are oriented parallel to long axis of nerve conduit to reach the distal end.

Figure 5:
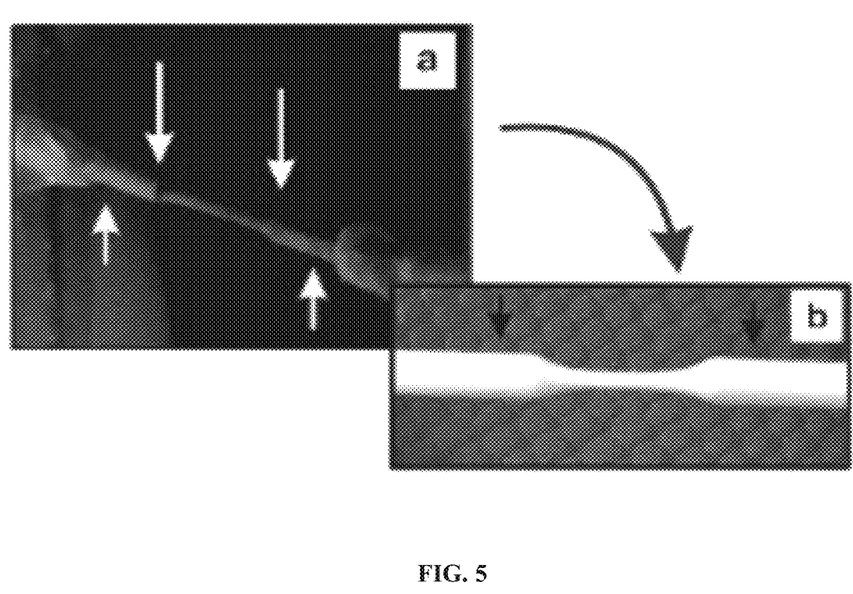
FIG. 5. illustrates a pictorial representation of the fibrous nerve conduit for promoting nerve regeneration, displaying (a) Image of electro-spinning collector during nerve conduit fabrication. (b) Image of nerve conduit before separation from collector.

Referring to FIG. 5, the random part is used to attach to the nerve stump due to its high mechanical strength and prevent conduit collapse during surgery and regeneration. During regeneration of damaged nerve, regenerated tissue filled the inner lumen of the conduit and bridged the gap between the two nerve stumps. As reported in different studies, the diameter of newly regenerated nerve would be smaller than proximal and distal nerve stumps and regenerated nerve is not completely cylindrical. Decreased lumen diameter at the middle length of the conduit showed that cylindrical structures with diameter of nerve stumps have a lot of dead space. Reduction in dead space could increase the growth factors concentration and improve both quality and quantity of axons regeneration.

Referring to FIGS. 1 and 5, to reduce dead space, the diameter of middle part decreased during electro-spinning of polymer on modified collector. As the electro-spinning start, straight fibers bridge the gap(produce aligned part of the conduit) and random nano-fibers cover the channel surface. Random nano-fibers can change the charge distribution on the surface of the channel and determine the deposition site for the next fibers. In the other word, the fibers that want to bridge between the gap, are permitted to deposit on the site with high charge density (lower nano-fiber density) so both end of the bridged fiber cannot be in the same plane. Thus the middle part is in the curved shape.

Figure 6:
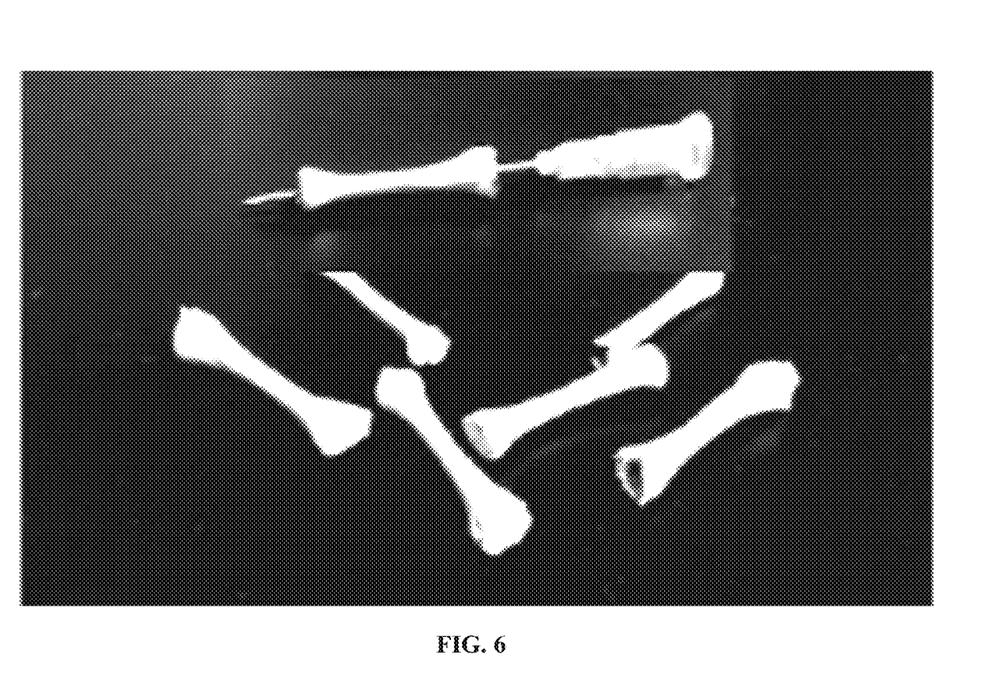
FIG. 6. illustrates a pictorial representation of the fibrous nerve conduit for promoting nerve regeneration. Showing nerve conduit.

Referring to FIG. 6, Difference in diameter between middle part and edge of the conduit resulted in the conical shape in both ends of the conduits. To match the size of the conduit with the size of the nerve, the conduit may cut from the ends to obtain appropriate diameter. Thus, one conduit may substitute the conduits with different sizes. A suture retention tests is performed on conduits produced by conventional air gap electro-spinning.

Figure 7:
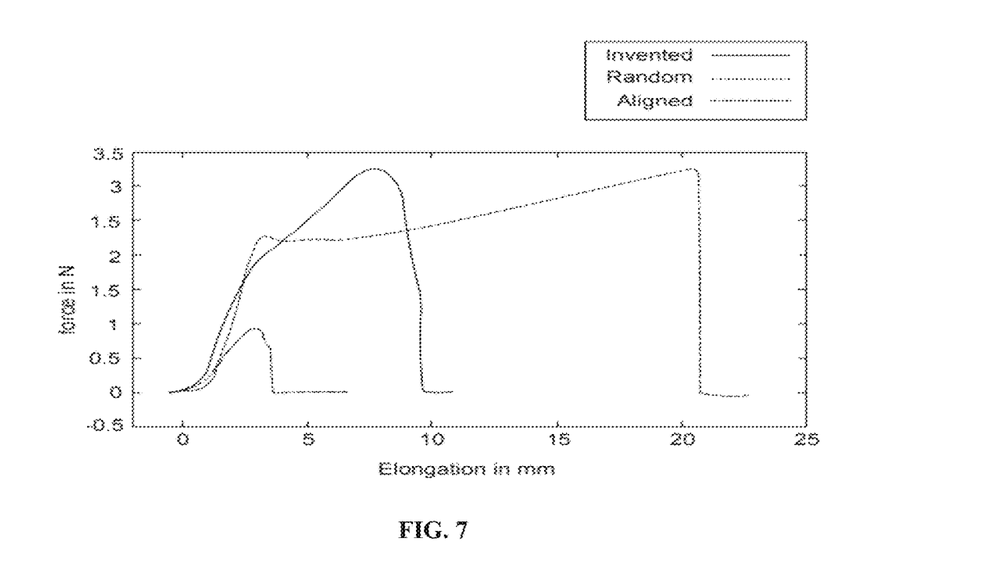
FIG. 7. illustrates a graphical representation of the fibrous nerve conduit for promoting nerve regeneration.
Figure 8:
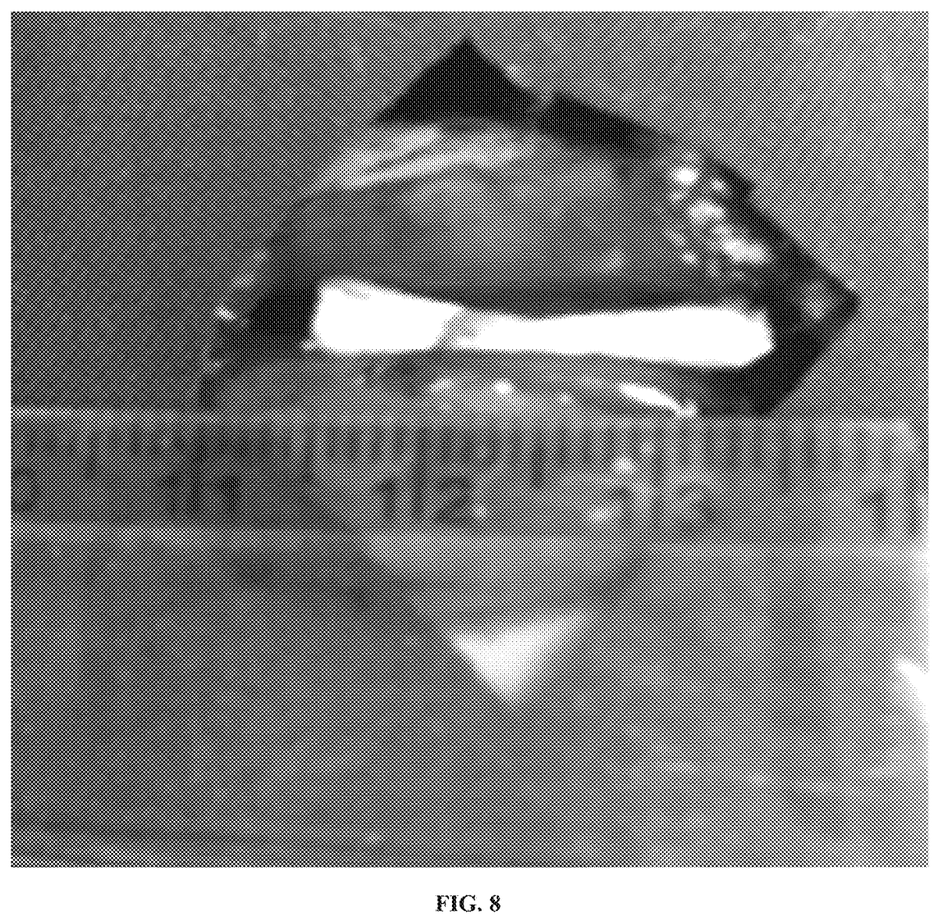
FIG. 8. illustrates a pictorial representation of the fibrous nerve conduit for promoting nerve regeneration, showing the conduit is sutured to proximal and distal ends of sciatic nerve.

Referring to FIG. 7, illustrates suture retention test, the results is shown by graphical representation. The elongation is shown in "mm" and the comparison is shown between the invented, random and aligned. The peak force achieved by aligned is around 1N and invented has achieved the force of around 3.3N. The random decreases slightly after reaching at 2.5N but it again raise to 3.3N.

To prepare the nerve conduit firstly a fibrous spinning solution is needed to be prepared. After that nano-fibers are produced by electro-s0.5-1.5) the solution prepared into the modified collector; and at last a conduit is separated.

Figure 9:
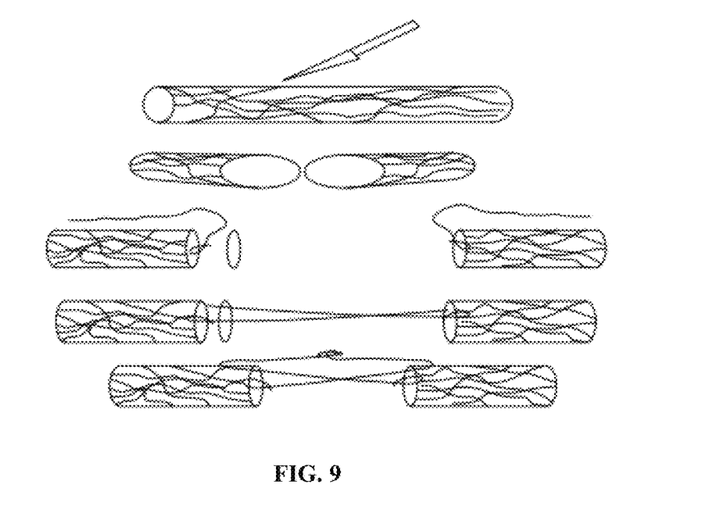
FIG. 9. illustrates a perspective view representing the method of surgery for installing the fibrous nerve conduit for promoting nerve regeneration.

Referring to FIG. 9, illustrates a perspective view representing the method of surgery for installing the fibrous nerve conduit for promoting nerve regeneration. The conduit is placed between the nerves in such a way that the two broken ends of the nerves connects with the ends of the conduit and then regenerate slowly.

Figure 10:
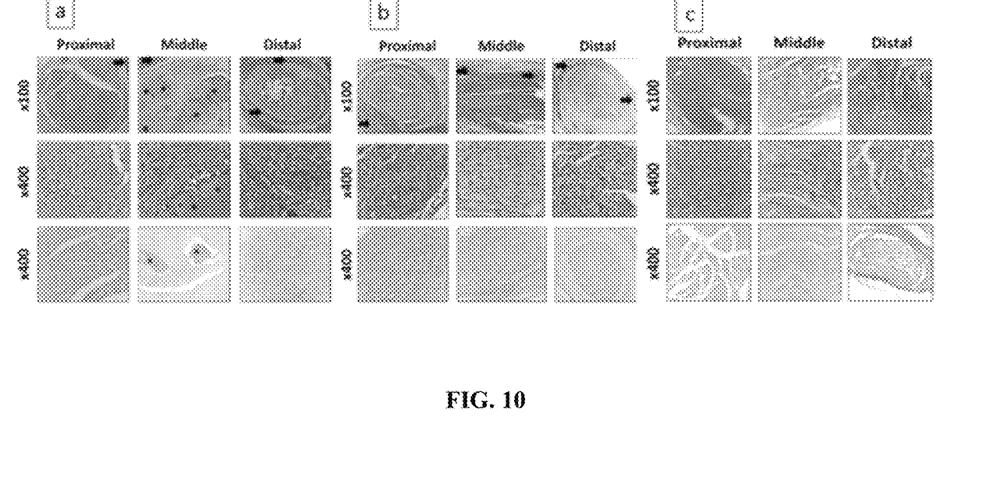
FIG. 10. illustrates a pictorial representation of the fibrous nerve conduit for promoting nerve regeneration.

Referring to FIG. 10, illustrated images of light micrographs of the sciatic nerve in three groups after nerve injury, H&E and LFB staining. The image shows the difference clearly between the three.

Example 1: The Preparation of PCL/Collagen nerve conduits. To prepare the electro-spinning solution, a homogeneous solution of PCL (12% w/v) (70 kDa: molecular weight, Sigma Chemical Co.) and collagen (10% w/v) (type I, Vista exir Co.) is obtained by dissolving PCL and collagen in HFIP. The solutions is mixed (50:50) and stirred for 1 h before electro-spinning. The clear solution is achieved and electro-spun from a 5 ml syringe with a needle gauge of 21 and flow rate of 1 ml/h. A high voltage (17 kV) is applied to the tip of the needle of the syringe. The distance between needle and collector is 15 cm and the size of gap is 2 cm. The conduit is fabricated by simultaneous deposition of the fibers both on channels and between them. The tubular constructs is removed by pulling the channel to the outside and let it to become dried for 24 hours prior for testing.

Example 2: The Preparation of PLGA/PCL-CNT nerve conduits. MWCNT (—COOH functionalized, diameter of 20-30 nm with a length of 10-30 μm) is purchased from US Research Nano material's, USA. A solution of PLGA (50 kDa, Esun Industrial Co.) (15%, w/v), PCL (10% w/v) and MWCNT (1 wt. % relative to PLGA/PCL) is prepared. In this regard, MWCNT is sonicated in HFIP for 4 h. Thereafter, PLGA and PCL polymers are dissolved and added to the dispersion solution of MWCNTs. The achieved solution is stirred for 4 hours and then, sonicated for 2 h before electro-spinning. The black viscose solution is achieved and electro-spun from a 5 ml syringe with a needle gauge of 21 and flow rate of 1 ml/h. A high voltage (15 kV) is applied to the tip of the needle of the syringe. The distance between needle and collector is 14 cm and the size of gap is 2 cm. The conduit is fabricated by simultaneous deposition of the fibers both on rods and between them. The tubular constructs are removed by pulling the rods to the outside and let it to become dried for 24 hours prior to testing.

Figure 3:
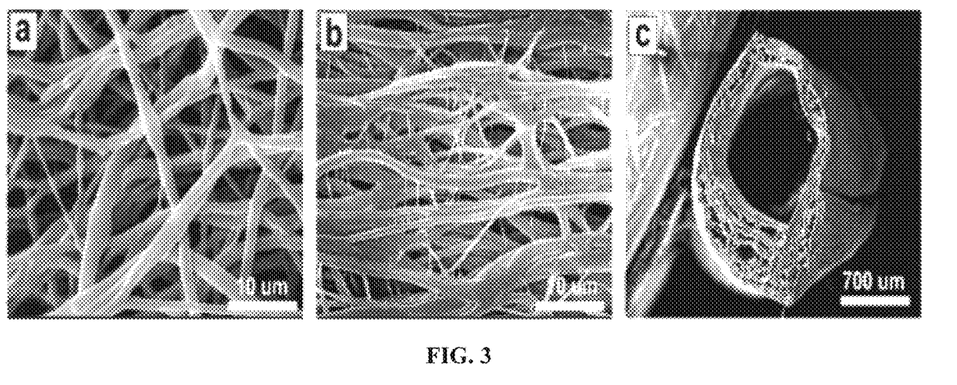
FIG. 3. illustrates a pictorial representation of the fibrous nerve conduit for promoting nerve regeneration, showing parts of fiber.

Example 3: Microscopic Imaging of nerve conduits. In this example, the microscopic imaging of conduits is performed in order to find out their structural characteristics. SEM images of PCL/Collagen nerve conduit of example 1. FIG. 3 demonstrates microscopic images of PLGA/PCL-CNT nerve conduit of example 2. The present invention has circle-shaped cross section and the inside of the conduit is hollow and the thickness of the nerve conduit is approximately 0.4-0.7 mm.

EXPERIMENT EXAMPLE 4: Measurement of Mechanical Properties. A suture retention test is performed following the ANSI/AAMI/ISO 7198:1998/2001/R2010 recommendations. Suture retention strength is one of the physical properties of nerve conduits and is evaluated by the nylon sutures placed in the conduit and the peak force measured during the pulling process. The sutures are pulled out at a constant rate of 50 mm/min. A force-elongation curve is prepared for three set of samples and the test repeated three times. One set of samples is referred to invented conduits of example 2. The second group composed of conduits with aligned nano-fibers and the last one composed of random nano-fibers. The invented nerve conduits revealed a superior tensile strength than conduits composed of aligned nano-fibers. Suture retention strength for the invented conduits is comparable to conduits from random nano-fibers but new design of conduits lead to significantly higher maximum elongation compared to both control nerve conduits (p<0.05). The suture retention strength of invented conduits, random conduit and aligned conduits are 3.5±0.5, 3.5±0.65 N and 1.12±0.3 N, respectively.

EXPERIMENT EXAMPLE 5: Measurement of Nerve Regeneration Effect. In this example, in Vivo nerve regeneration with new design conduits is described. Rats are divide into 5 groups as described in table.

| | Rats group name | | | | |
|---|---|---|---|---|---|
| | 1 | 2 | 3 | 4 | 5 |
| characteristic | Negative control | Autograft | Conduit with aligned fibers | Conduit with random fibers | Conduit with invented design |

Anesthesia is employed by an intra-peritoneal (i.p.) injection of ketamine (80 mg/kg) and xylazine (10 mg/kg). After anesthesia is administered fur is removed from the hindquarters, and skin is swabbed with betadine. To start surgery, skin and muscle overlaying the sciatic nerve are mobilized, and a 15 mm segment of the nerve is removed. The both end of nerve stumps are fixed with one suture and inserted to the nerve conduit using 6-0 nylon sutures. Aligned nerve conduits collapsed during surgery and damaged nerve stumps could not insert in the conduits and surgery in group 3 stopped. At the end of surgery, skin incisions are stapled and the animals are allowed to recover. After surgery all animals are given free access to water and food and housed in cage. 12 weeks after the surgery, the sciatic nerve in the place of the graft is dissected out and fixed in the 10% neutral buffered formalin (NBF, PH. 7.26) for 48 h. The harvested tissue samples processed, embedded in paraffin blocks and cut into 5 mm thick sections. For the nerve specimens, transverse (proximal and distal parts) and longitudinal (middle part) sections are obtained from the sciatic nerve (cutting area). All nerve sections are made in duplicate: the first one is stained with haematoxylin and eosin (H&E) and the second by luxol fast blue (LFB). Finally, the histological slides are evaluated by the independent reviewer, using light microscopy (Olympus BX51; Olympus, Tokyo, Japan).

After placing the fibrous conduit between the broken nerve, that leads to growth in the branches of the broken nerve. Hence regeneration of nerve takes place without facing the problem of size compatibility.

Although the field of the invention has been described herein with limited reference to specific embodiments, this description is not meant to be construed in a limiting sense. Various modifications of the disclosed embodiments, as well as alternate embodiments of the invention, will become apparent to persons skilled in the art upon reference to the description of the invention.

We claim:

1. A fibrous nerve conduit for promoting nerve regeneration, comprising a channel that attaches to a proximal and distal end of a severed nerve, wherein the fibrous nerve conduit comprises electrospun polycaprolactone-poly(L-lactic co glycolic acid)-carbon nanotube (PCL-PLGA-CNT) nanofibers, and wherein the concentration of PCL in the fibrous nerve conduit is in the range of 10-15% (w/v) and the concentration of PLGA in the fibrous nerve conduit is in the range of 10-18% (w/v).

2. The fibrous nerve conduit of claim 1, wherein the PCL-PLGA-CNT nanofibers each comprise about 10 to 90% by weight PCL and about 90 to 10% by weight PLGA.

3. The fibrous nerve conduit of claim 1, wherein the PCL-PLGA-CNT nanofibers have a diameter in the range of 100-800 nm.

4. The fibrous nerve conduit of claim 1, wherein the channel has a proximal and distal end that is conical in shape.

5. The fibrous nerve conduit of claim 1, wherein the channel is cylindrical in shape.

6. The fibrous nerve conduit of claim 1, wherein the fibrous nerve conduit further comprises a protein.

7. The fibrous nerve conduit of claim 1, wherein the fibrous nerve conduit further comprises a drug.

8. A method for promoting the regeneration of a nerve comprising placing the fibrous nerve conduit of claim 1 in between the broken ends of a nerve.

* * * * *